US00PP36528P3

(12) United States Plant Patent
Schoone

(10) Patent No.: US PP36,528 P3
(45) Date of Patent: Mar. 4, 2025

(54) ***PHALAENOPSIS* PLANT NAMED 'GLITZY'**

(50) Latin Name: *Phalaenopsis hybrida*
Varietal Denomination: GLITZY

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/735,110

(22) Filed: Jun. 5, 2024

(65) Prior Publication Data

US 2024/0415038 P1 Dec. 12, 2024

Related U.S. Application Data

(60) Provisional application No. 63/471,471, filed on Jun. 6, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Glitzy', characterized by its upright plant habit; moderately vigorous growth habit; strong flowering stems; strong leaves; freely flowering habit with typically two inflorescences developing per plant, each inflorescence with numerous flowers; flowers with reddish purple-colored petals and sepals with darker reddish purple-colored venation; and good postproduction longevity.

2 Drawing Sheets

Figure 1:
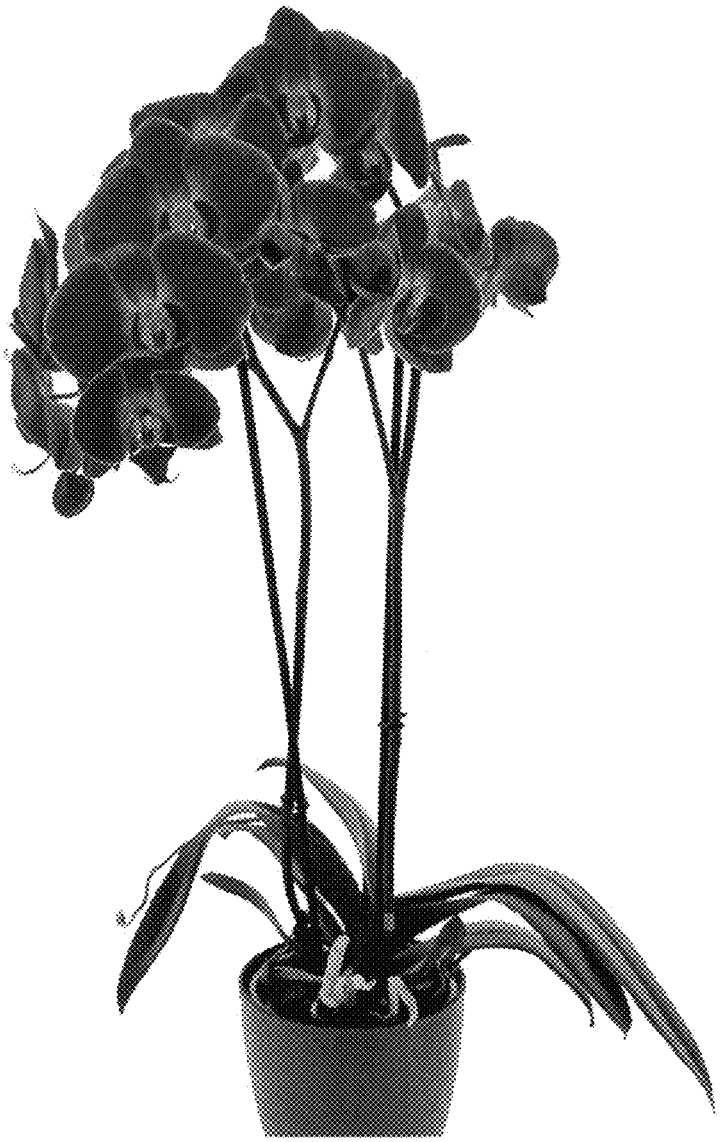

Botanical designation: *Phalaenopsis hybrida.*
Cultivar denomination: 'GLITZY'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Floricultura B.V. of Heemskerk, The Netherlands on Feb. 27, 2023, application number 2023/0519. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Glitzy'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in January, 2013 in Assendelft, The Netherlands of *Phalaenopsis hybrida* 'Chain Xen Piano', not patented, as the female, or seed, parent with *Phalaenopsis hybrida* 'Fuller's Light', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in January, 2020.

Asexual reproduction of the new *Phalaenopsis* plant by in vitro meristem propagation in a controlled environment in Assendelft, The Netherlands since January, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Glitzy'. These characteristics in combination distinguish 'Glitzy' as a new and distinct *Phalaenopsis* plant:

1. Upright plant habit.
2. Moderately vigorous growth habit.
3. Strong flowering stems.

4. Strong leaves.
5. Freely flowering habit with typically two inflorescences developing per plant, each inflorescence with numerous flowers.
6. Flowers with reddish purple-colored petals and sepals with darker reddish purple-colored venation.
7. Good postproduction longevity.

Plants of the new *Phalaenopsis* can be compared to plants of the female parent, 'Chain Xen Piano'. Plants of the new *Phalaenopsis* differ primarily from plants of 'Chain Xen Piano' in flower color as petals and sepals of plants of the new *Phalaenopsis* are reddish purple in color with darker reddish purple-colored venation whereas petals and sepals of plants of 'Chain Xen Piano' are white tinged with soft yellow in color with a few purplish red-colored spots.

Plants of the new *Phalaenopsis* can be compared to plants of the male parent, 'Fuller's Light'. Plants of the new *Phalaenopsis* differ primarily from plants of 'Fuller's Light' in flower color as petals and sepals of plants of the new *Phalaenopsis* are reddish purple in color with darker reddish purple-colored venation whereas petals and sepals of plants of 'Fuller's Light' are reddish purple in color with a moderate amount of purplish red-colored spots.

Plants of the new *Phalaenopsis* can be compared to plants of *Phalaenopsis hybrida* 'Purple Dust', disclosed in U.S. Plant Pat. No. 29,177. In side-by-side comparisons, plants of the new *Phalaenopsis* differ primarily from plants of 'Purple Dust' in the following characteristics:

1. Dorsal sepals of plants of the new *Phalaenopsis* are broader than dorsal sepals of plants of 'Purple Dust'.
2. Petals and sepals of plants of the new *Phalaenopsis* are reddish purple in color with darker reddish purple-colored venation whereas petals and sepals of plants of 'Purple Dust' are purple violet with a white haze in the center.
3. Cirrhose tips of plants of the new *Phalaenopsis* are purplish red in color whereas cirrhose tips of plants of 'Purple Dust' are white in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Glitzy' grown in a container.

Figure 2:
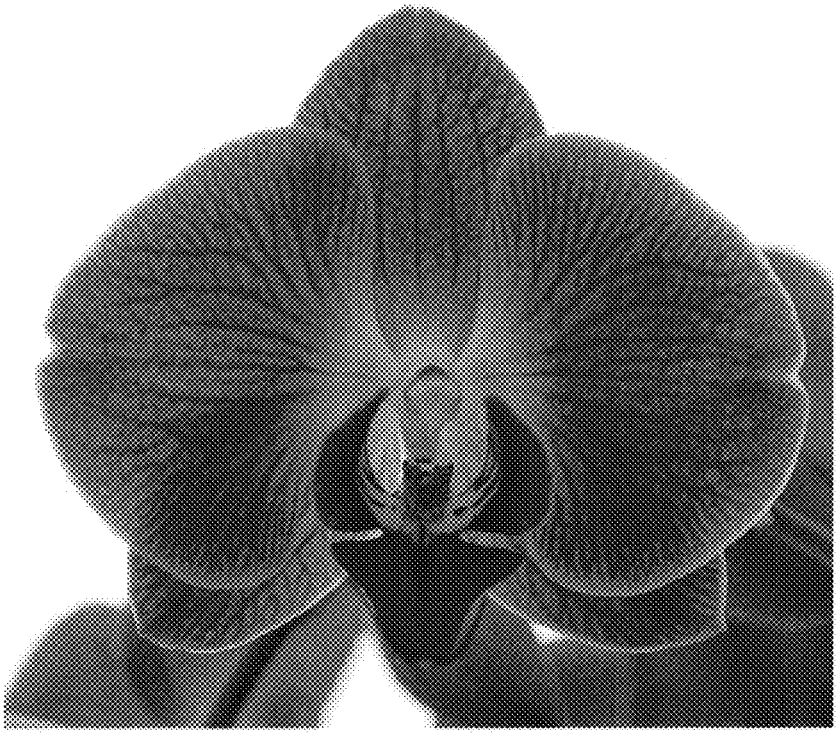

The photograph on the second sheet (FIG. 2) is a close-up view of a typical flower of 'Glitzy'.

DETAILED BOTANICAL DESCRIPTION

The aforementioned photographs and following observations and measurements describe plants grown during the winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Glitzy'.

Parentage:

*Female, or seed, parent.*—*Phalaenopsis hybrida* 'Chain Xen Piano', not patented.

*Male, or pollen, parent.*—*Phalaenopsis hybrida* 'Fuller's Light', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 13.6 cm.

*Plant height, substrate level to top of floral plane.*—About 50.3 cm.

*Plant diameter or spread.*—About 35.3 cm.

Leaf description:

*Arrangement and quantity.*—Distichous, simple; sessile; about eight fully-developed leaves per plant.

*Length.*—About 24.2 cm.

*Width.*—About 7.5 cm.

*Aspect.*—Semi-erect to somewhat outwardly arching.

*Shape.*—Narrowly elliptic-oblong to narrowly obovate; slightly carinate; slightly reflexed.

*Apex.*—Unequal acute.

*Base.*—Sheathing. Sheath length: About 2.1 cm. Sheath width: About 1.8 cm. Sheath color, upper and lower surfaces: Close to 143B.

*Margin.*—Entire.

*Texture and luster, upper and lower surfaces.*—Smooth, glabrous; slightly glossy.

*Venation pattern.*—Camptodromous.

*Color.*—Developing leaves, upper surface: Close to NN137A. Developing leaves, lower surface: Close to 146A; proximally, marginal edges strongly tinged with close to N186C. Fully expanded leaves, upper surface: Close to NN137B; marginal edges, close to 137A; venation, close to NN137B. Fully expanded leaves, lower surface: Close to NN137B; towards the base, close to 146B; venation, close to NN137D.

Inflorescence description:

*Appearance and flowering habit.*—Showy zygomorphic flowers arranged on axillary simple or branched racemes; typically two inflorescences develop per plant; each inflorescence with about 15 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 29.6 cm.

*Inflorescence width*.—About 21.7 cm.

*Flower buds, about one week before opening*.—Height: About 1.9 cm. Diameter: About 1.8 cm. Shape: Broadly ovate. Color: Close to N77B; towards the base, tinged with close to 148D.

*Flower size*.—About 7.4 cm (vertical) by 8.7 cm (horizontal).

*Flower depth*.—About 3.1 cm.

*Petals, quantity and arrangement*.—Three, two lateral petals and one center petal transformed into a labellum.

*Lateral petals*.—Length: About 4.1 cm. Width: About 5.3 cm. Shape: Broadly deltoid-reniform to roughly lunate. Apex: Retuse. Margin: Entire; not undulate. Texture and luster, upper and lower surfaces: Smooth, glabrous; moderately velvety; matte. Color: When opening, upper surface: Close to NN78B; towards the base, close to NN155B; narrow marginal edges, close to 76B to 76C; venation, close to N78A. When opening, lower surface: Close to N78C; towards the center, close to N75C and N75D; towards the base, close to 157A and 157B; venation, close to N78A. Fully opened, upper surface: Close to a blend of N78B and NN78B; towards the base, close to N155A; narrow marginal edges, close to 76C; venation, close to N78A; colors do not change with subsequent development. Fully opened, lower surface: Close to N78C; towards the center, close to N78D; towards the base, close to N155A; venation, close to N78B; colors do not change with subsequent development.

*Labella*.—Appearance: Three-parted with two lateral lobes and a central lobe. Length, lateral lobes: About 2.1 cm. Width, lateral lobes: About 1.5 cm. Length, central lobe: About 2.4 cm. Width, central lobe: About 0.5 cm to 2.4 cm. Length, cirrhose tips: About 1.5 cm. Shape, lateral lobes: Obovate. Shape, central lobe: Deltoid with an elongated apex. Apex, lateral lobes: Obtuse. Apex, central lobe: Cleft with two upright and backwardly curled cirrhose tips. Margins, lateral lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 6 mm in width and about 6 mm in height. Color: When opening, upper surface: Lateral lobes: Close to a blend of N78A and NN78A; towards the base, close to NN155A; axial stripes, close to 71A. Central lobe: Close to NN78B; towards the base, close to 157A; main vein, close to N78A; radial stripes, close to 60A; cirrhose tips, close to NN78B. When opening, lower surface: Lateral lobes: Close to 77B and 77C with irregular marbling, close to 76A and 76B; proximal marginal edges, close to NN74B; at the base, close to 155C. Central lobe: Close to NN78B; towards the base, close to 72A and at the base, close to 157A; cirrhose tips, close to NN78A. Fully opened, upper surface: Lateral lobes: Close to a blend of N78A and NN78A; towards the margins, close to N78A; at the base, close to NN155B; axial stripes, close to 71A. Central lobe: Close to a blend of NN78B and NN78C; towards the base, close to NN78B and at the base, close to 157D; main vein, close to N78A; radial stripes, close to 60A; cirrhose tips, close to NN78B. Fully opened, lower surface: Lateral lobes: Close to N78A with irregular marbling, close to 76A; proximal marginal edges, close to 71A; at the base, close to 156D. Central lobe: Close to 77C; towards the base, close to N78A and N78B and at the base, close to 157A; cirrhose tips, close to N78A and N78B. Callosities: When developing: Close to 154B with fine dots, close to 59B. Fully developed: Close to 12C with fine dots, close to 59A.

*Sepals*.—Quantity and arrangement: Three, one upper dorsal sepal and two lower lateral sepals. Length, dorsal sepal: About 4.3 cm. Width, dorsal sepal: About 3.4 cm. Length, lateral sepals: About 4.2 cm. Width, lateral sepals: About 2.7 cm. Shape, dorsal sepal: Broadly elliptic. Shape, lateral sepals: Ovate. Apex, dorsal sepal: Obtuse to shallowly retuse. Apex, lateral sepals: Bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to N78C; towards the base, close to 157D; narrow marginal edges, close to 76C to 76D; venation, close to N78A. When opening, lower surface: Close to 186A and 186B; towards the apex and margins, close to N78C; narrow marginal edges, close to 76C to 76D; venation, close to 71A. Fully opened, upper surface: Close to a blend of N78B and NN78B; towards the base, close to N155A; narrow marginal edges, close to 76C; venation, close to N78A. Fully opened, lower surface: Close to N78B; towards the center, tinged with close to 72A; at the base, close to 156D; narrow marginal edges, close to 76C; venation, close to 71A. Color, lateral sepals: When opening, upper surface: Close to N78C; towards the base, close to 157D; narrow marginal edges, close to 76C; venation, close to N78A. When opening, lower surface: Close to 186A and 186B; towards the apex and margins, close to N78C; towards the base, flushed with close to 195B; narrow marginal edges, close to 76C to 76D; venation, close to 187B. Fully opened, upper surface: Close to a blend of N78B and NN78B; towards the base, close to 156C and 156D; narrow marginal edges, close to 76C; venation, close to N78A. Fully opened, lower surface: Close to N78B; towards the center, tinged with close to 72A; at the base, close to 156D; narrow marginal edges, close to 76C; venation, close to 71A.

*Peduncles*.—Length: About 56.6 cm. Diameter: About 6 mm. Strength: Strong. Aspect: Upright to outwardly arching. Texture and luster: Smooth, glabrous; matte. Color: Close to 146A covered with fine dots, close to 197A.

*Pedicels*.—Length: About 4 cm. Diameter: About 3 mm. Strength: Moderately strong. Aspect: About 60° from peduncle axis. Texture and luster: Smooth, glabrous; matte. Color: Close to 186C; proximally, tinged with close to 200B and 200C.

*Reproductive organs*.—Androecium: Column length: About 9 mm. Column width: About 6 mm. Column color: Close to N78A; proximally, close to 76D; distally, close to NN155A. Pollinia quantity: Two. Pollinia diameter (per two pollinia): About 2.5 mm. Pollinia color: Close to 25B. Gynoecium: Stigma length: About 3 mm. Stigma width: About 4 mm. Stigma shape: Reniform. Stigma color: Close to N155A. Ovary length: About 8 mm. Ovary diameter: About 1 mm. Ovary color: Close to 149A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Glitzy' as herein illustrated and described.

* * * * *